United States Patent [19]
Patzke

[11] Patent Number: 5,402,682
[45] Date of Patent: Apr. 4, 1995

[54] ROTOR OF AN ULTRASONIC TEST DEVICE FOR ROTATIONALLY SYMMETRICAL TEST SPECIMENS, ESPECIALLY TUBES

[75] Inventor: Ottokar Patzke, Erftstadt, Germany

[73] Assignee: Krautkramer GmbH & Co., Germany

[21] Appl. No.: 859,720

[22] PCT Filed: Jun. 29, 1991

[86] PCT No.: PCT/DE91/00543
§ 371 Date: Aug. 28, 1992
§ 102(e) Date: Aug. 28, 1992

[87] PCT Pub. No.: WO92/01221
PCT Pub. Date: Jan. 23, 1992

[30] Foreign Application Priority Data
Jul. 3, 1990 [DE] Germany .................. 9010086 U

[51] Int. Cl.⁶ .................................. G01N 29/26
[52] U.S. Cl. .................................. 73/622; 73/621
[58] Field of Search ............... 73/618, 619, 620, 621, 73/622, 627, 629, 632, 633, 634, 640, 635

[56] References Cited
U.S. PATENT DOCUMENTS
3,789,656 2/1974 Miller ........................... 73/635

Primary Examiner—Richard E. Chilcot, Jr.
Assistant Examiner—Joseph L. Felber
Attorney, Agent, or Firm—Eckert Seamans Cherin & Mellott

[57] ABSTRACT

An ultrasonic test device for rotationally symmetrical test specimens permits performing oblique error testing. A probe carrier is mounted within a bore hole of a rotor such that its position can be rotationally adjusted about the axis of the bore hole and also adjusted longitudinally in the direction of the axis of the bore hole. Thus, especially in combination with an angle probe or an inclination-adjustable probe, the acoustic irradiation angle can be adjusted by rotation of the probe carrier. In this way, it is possible to achieve test paths for rotors that range continuously between every test spiral pitch.

16 Claims, 2 Drawing Sheets

ROTOR OF AN ULTRASONIC TEST DEVICE FOR ROTATIONALLY SYMMETRICAL TEST SPECIMENS, ESPECIALLY TUBES

BACKGROUND OF THE INVENTION

1. Field of the Invention

The invention pertains to a rotor of an ultrasonic test device for rotationally symmetrical test specimens, especially tubes, in which the rotor holds a probe carrier, which a) is arranged in a radial borehole, b) contains at least one probe, c) is mounted in such a way that it can be moved longitudinally in the direction of the axis of the borehole, and d) is tightly sealed in the borehole.

2. Prior Art

Test devices of this type are already well known for testing along the entire length of the test specimen and/or only for testing the end regions of a test specimen. Testing over the entire length of the test specimen is generally performed in continuous operation; the rotor remains fixed in its position as it rotates, and the test specimen is moved axially through the rotor along its longitudinal axis. For general information on the state of the art, the reader is referred to the book: J. and H. Krautkrämer, Werkstoffprüfung mit Ultraschall [Material Testing with Ultrasound], 5th Ed., Springer Verlag, especially the section entitled "Tubes," which describes test systems for tubes.

Test devices of this kind are intended for rotationally symmetric test specimens of a general type, including not only round material, especially tubes and bars, but also material with regular polygonal cross sections, such as hexagonal bars. In this connection, see DE-A-38 03 151 and the unpublished document DE-A-39 08 967.

A rotor of the type mentioned above is used in the prior-art rotation test system for tubes between 20 and 180 mm in diameter, type ROT 180, manufactured by Krautkrämer GmbH & Co. Its two end regions are sealed from the test specimens in such a way that the central borehole of the rotor can be filled with water or other suitable probe-to-specimen contact fluid. The probe carrier is movably mounted in a radial borehole of the rotor arranged transverse to the axis of the test specimen. The probe carrier itself is designed as a type of piston. Test specimens of varying diameters can be systematically positioned by radial movement. In addition, the probe can be retracted to a protected position before a test specimen is run in. The central borehole is also sealed radially towards the outside, in the region of the probe carrier, by a seal between the borehole and the probe carrier. This also prevents contact fluid from escaping radially to the outside.

This previously known device can detect longitudinal and cross-sectional errors, and wall thickness can also be determined. Oblique errors in the test specimen cannot be reliably determined.

SUMMARY OF THE INVENTION

This is where the invention comes in. The goal of the invention was to modify the previously known rotor of the type described above in such a way that, in addition to the existing testing possibilities, it would also be possible to perform oblique error testing in ultrasonic rotation test systems.

This goal is accomplished by mounting the probe carrier within the borehole in such a way that it can be rotationally adjusted about the axis of this borehole. Rotation of the probe carrier in its borehole was neither possible nor suitable in the state of the art, since in the previously known alignment of the probes, no physical effect was achieved by a rotation. However, especially in combination with an angle probe or an inclination-adjustable probe, the acoustic irradiation angle can be additionally adjusted by the rotation of the probe carrier. In this way, it is possible to achieve test paths for rotors that range continuously between every test spiral pitch (between pure cross-sectional testing with circular test path and pure longitudinal testing with a test path in the longitudinal direction).

In a preferred modification, the inclination of the probe can be adjusted about an axis of rotation transverse to the axis of the borehole of the rotor, the probe has a first screw part located outside of this axis of rotation, and this first screw part is associated with a second screw part, which extends in the direction of the axis of the borehole and which is connected with a rotation adjustment device accessible on the outside of the probe carrier.

These measures make it possible to adjust the inclination of the probe inside the probe carrier. The design we have described is suitable for the high centrifugal accelerations that arise in the region of rotors. Reproducible inclination adjustment is accomplished from the curved outer surface of the rotor. It is desirable to attach the rotation adjustment device to a scale, from which the adjusted angle can be directly read. The rotation adjustment device transfers the adjustment motion to the second screw part, which is preferably designed as a spindle supported in the probe. This in turn is connected with the first screw part, which transfers the adjustment motion to the probe.

In a preferred modification, the axis of rotation of the probe intersects the borehole axis at right angles. This results in simplified adjustment of the acoustic irradiation angle in the case of combined adjustment by rotation of the probe carrier and inclination of the probe.

It has also been found to be advantageous to install the probe centrally on the axis of the borehole of the rotor. This also simplifies the adjustment of the acoustic irradiation angle.

On the other hand, by arranging the probe a certain distance from the axis of the borehole and/or by arranging the axis of rotation a certain distance from this axis of the borehole, acoustic irradiation angles and sites can be adjusted for special jobs, which cannot be achieved with the above-described arrangement of the probe centrally on the borehole axis and an axis of rotation that intersects the axis of the borehole. Adjustment to different test specimen diameters is still necessary.

In a preferred design, the probe (in the physical sense) is designed with an L-like shape. It has a first L-leg, which holds an ultrasonic element, and a second L-leg, on which the first screw part is mounted. This system can be jointed, but it is also possible to design the first screw part as a toothed segment, in which case it is rigidly connected with the second leg, preferably as a single piece. The two legs are arranged at right angles to each other. The outer shape of the probe can be disklike, segmented, L-shaped or the like.

Other advantages and features of the invention are apparent from the subclaims and from the following description of three specific embodiments of the invention, which are understood to be examples that in no way limit the invention. These embodiments are explained in detail with reference to the drawings.

DESCRIPTION OF THE PREFERRED EMBODIMENTS

Figure 1:
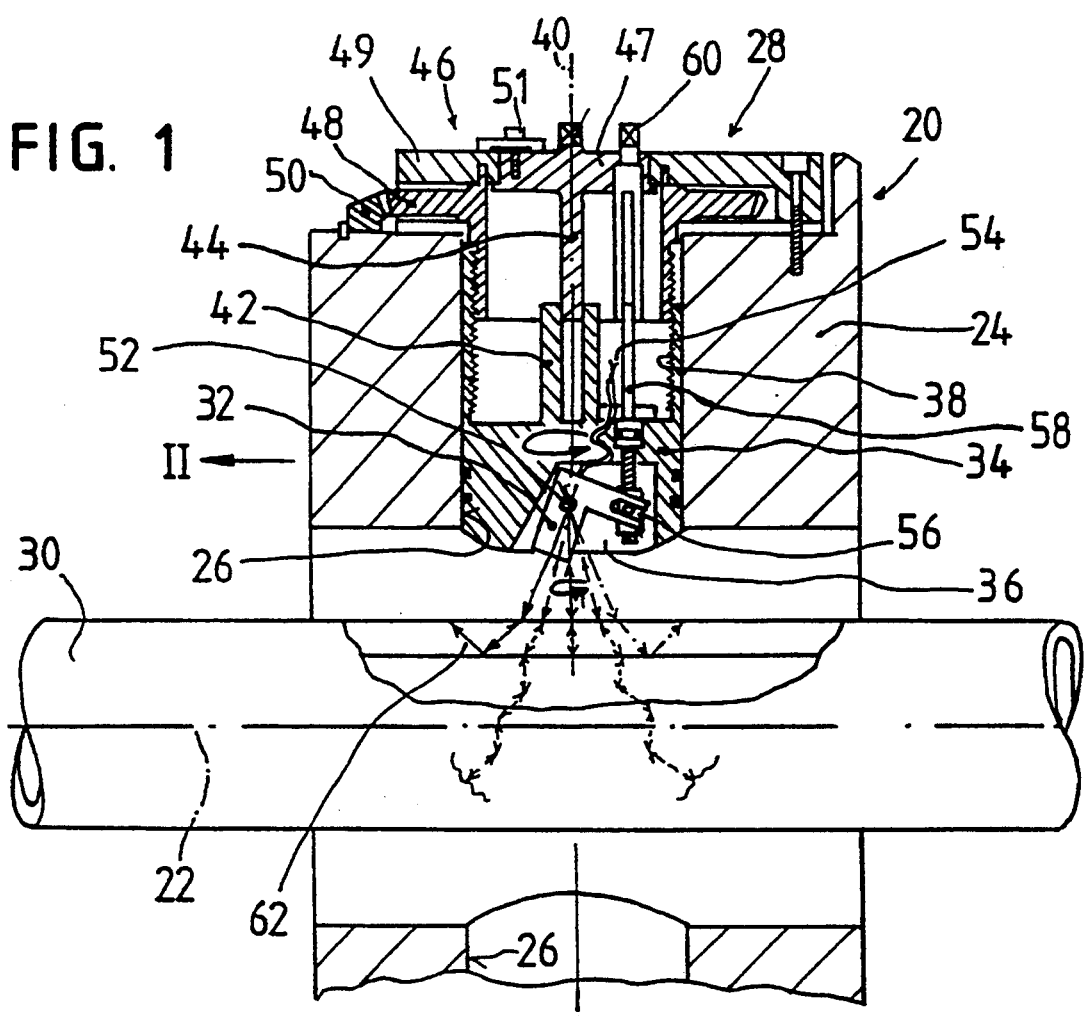
FIG. 1 shows a radial cross section through a rotor (partial) with a test specimen in the form of a tube.
Figure 2:
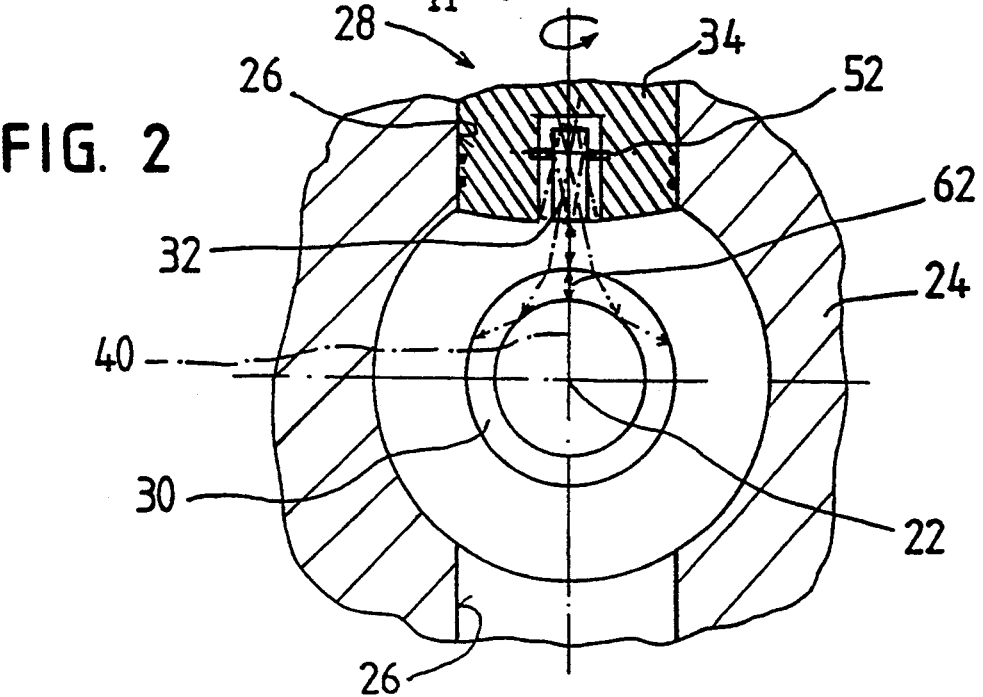
FIG. 2 shows a cross section in the direction of intersecting line II—II in FIG. 1.

In the first embodiment of the invention, which is illustrated in FIGS. 1 and 2, there is a rotor 20, which can be turned about an axis of rotation 22 by a well-known device. It has a rotor body 24, which is provided with two exactly opposite radial boreholes 26. The upper borehole 26 is filled with a probe carrier 28, which basically has the form of a cylindrical piston. A probe 32 is mounted in its lower side (in FIG. 1), which faces a test specimen 30 in the form of a tube. The space between the rotor 20 and the test specimen 30 is filled in an already well-known way with a contact fluid, which is not shown in the drawings.

The probe carrier 28 consists of an essentially cup-shaped main piece 34, whose thickened base has a chamber 36, which opens downward towards the test specimen 30, for holding the probe 32. In the upward direction, the main piece 34 is tubular, and the inside wall of the tube is provided with threading 38. In addition, a tube piece 42 extends upward from the thickened base centrically to the axis 40 of the borehole 26. It has a noncircular inner cross section, e.g., a slot, a square hollow profile or the like. A correspondingly shaped driver 44 fits into this noncircular inner cross section. The driver 44 extends downward as a single piece from a multipart flange 46. When the flange 46 is turned, the cup-shaped main piece 34 is also turned. Differences in distance between the two parts 34 and 46 are compensated by the driver 44 moving more or less deeply into the tubular piece 42 without the coupling between the tube 42 and the driver 44 being lost.

In the example shown here, the flange 46 is designed in two parts, a disk 47 and a ring 49. The ring is a stationary part. It is fixed by a screw, as FIG. 1 shows. The centric disk 47 can be turned. It supports the driver 44, and its extension on the outside has a square end. An adjusted angular position of the disk 47 is secured relative to the ring 49 by means of a claw 51.

Between the flange 46 and the main piece 34, there is a counterpart 48, which is essentially overlapped by the ring 49 of the flange 46 and has a downwardly directed tubular part, which has external threading corresponding to the internal threading 38. If this counterpart 48 is fixed, but the disk 47 of the flange 46 is turned, the main piece 34 and the probe 32 turn about the axis 40 of the borehole 26, thus producing a changed angular position of the main piece 34 inside the borehole. By rotation of the counterpart 48, which has external gearing that engages a gear ring 50, which runs around the rotor, the main piece 34 can be moved in the direction of the axis 40 of the borehole 26. This changes the distance of the probe 32 from the test specimen without changing the angular position. If both the counterpart 48 and the flange 46 are turned, the angular position of the main piece 34 inside the borehole 26 changes without any change in the axial distance. Scales (not shown) are provided for both of the above-described adjusting movements.

Physically, the probe has an L-shaped design. Inside the chamber 36, the probe is mounted in such a way that it can turn about an axis 52 within an angular range. This axis of rotation 52 intersects the axis 40 of the borehole at right angles. The downwardly directed leg in FIG. 1 is equipped with an ultrasonic element (not shown in detail here), which is powered by an electric power line 54. The other leg forms a fork, which holds the pin of a nut, which constitutes a first screw part 56. This engages a spindle, which embodies a second screw part 58. The spindle is pivoted in the thickened base of the main piece 34; it runs parallel to the axis 40 of the borehole 26 at a distance from this axis. It is sealed by a gasket. It continues upward into a variable-length coupling. The spindle 58 that forms the second screw part can be turned by means of a square end 60 that is accessible from the outside, which causes a change in the inclination of the probe 32. This is indicated in FIGS. 1 and 2 by different arrows. The solid-line arrows 62 describe the path of the sound for the present angular position, and the broken-line arrows belong to different, changed angular positions of the probe 32.

As FIG. 1 shows, the probe 32 can be turned clockwise through an angle of about 35° from the vertical, in which the axis 40 passes centrically through its first leg. In addition, it can be turned counterclockwise beyond the vertical position (towards the right in FIG. 1).

Basically, however, angular movement in one direction is sufficient, since the inclination in the other direction (towards the right in FIG. 1) is obtained by rotating the main piece 34 by 180°.

In the above-described embodiment of the invention shown in FIGS. 1 and 2, the probe carrier 28 is mounted in a borehole 26 of the rotor. The following embodiments of the invention refer to designs in which several probe carriers 28 are mounted in a borehole 26 of a support 68, which in turn is inserted radially in the rotor 20. In the illustrated embodiments of the invention, boreholes 70 are provided in the rotor 20, one borehole for each such support 68.

Figure 3:
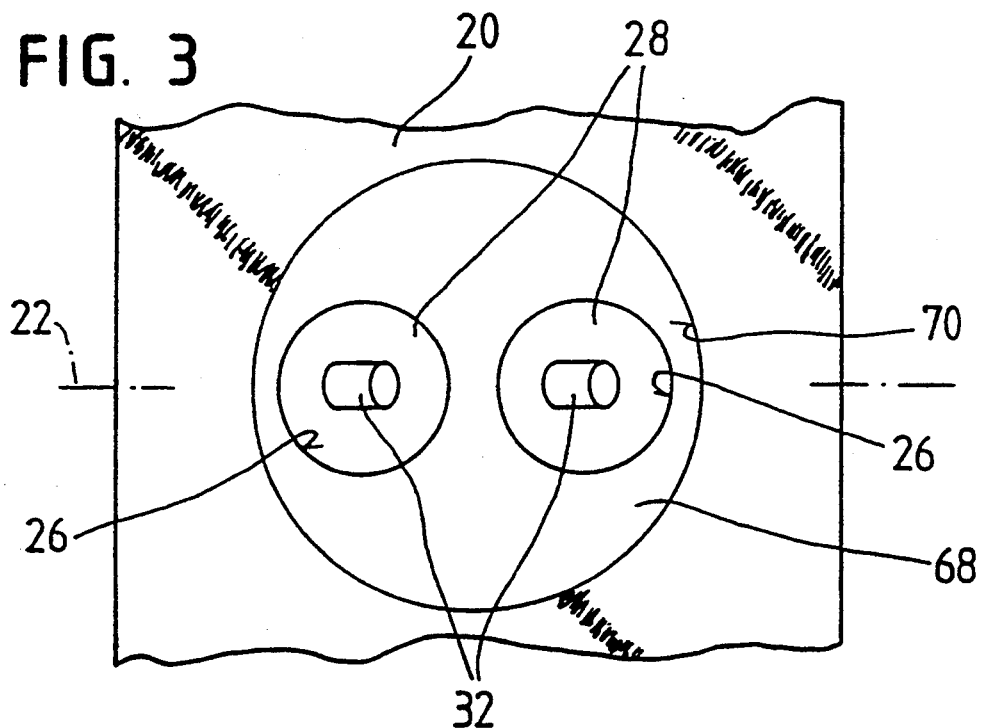
FIG. 3 shows a bottom view of a support arranged in a radial borehole of a rotor, in which two probe carriers are mounted in such a way that they can be rotationally adjusted.
Figure 4:
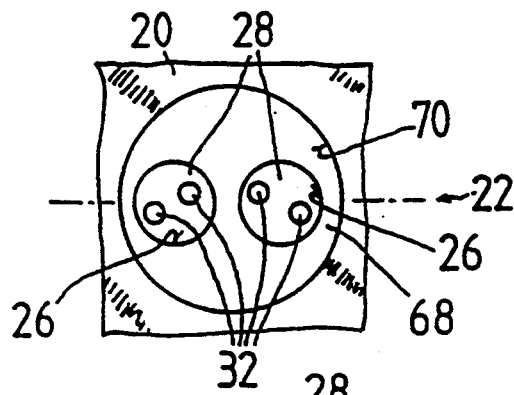
FIG. 4 is a drawing corresponding to FIG. 3, in which each probe carrier has two probes.
Figure 5:
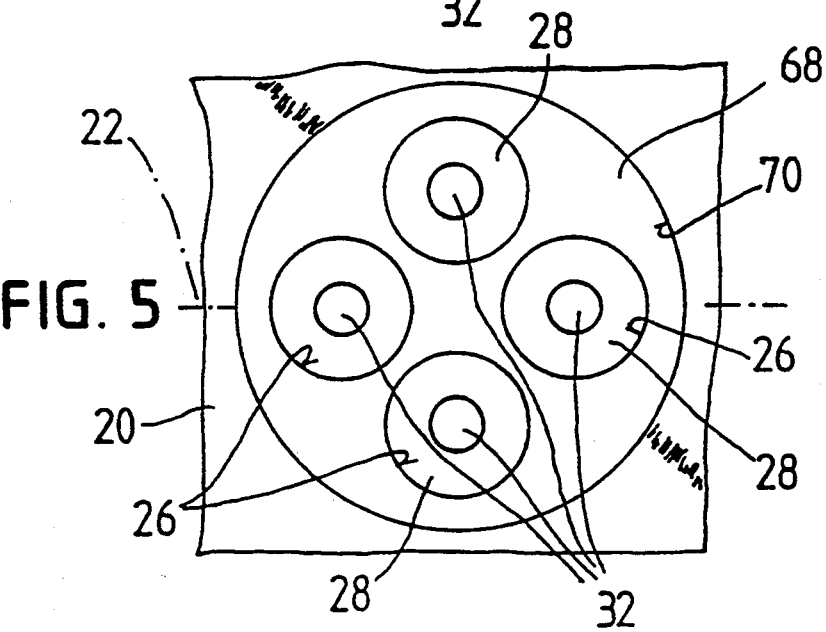
FIG. 5 is a drawing corresponding to FIG. 3, but with a support in which four probe carriers are mounted.

The probe carriers 28 in the embodiments of the invention shown in FIGS. 3 to 5 can be designed the same as the probe carriers 28 of the embodiment of the invention shown in FIGS. 1 and 2, i.e., axially movable and rotationally adjustable about the axis 40. At the same time, the support can also have one of these functions. It is desirable to design it so that it can be turned about the axis of the borehole 70. Axial adjustability inside the borehole 70 is also desirable.

At least one probe 32 is mounted in each probe carrier 28. This does not necessarily have to be angularly adjustable, as in the example of the invention shown in FIGS. 1 and 2, but rather probes with fixed angular characteristics can be used, e.g., probes with an angle of 30° to the axis 40.

In a typical design, the probes 32 are adjusted in such a way that they are directed at a point of the surface of the test specimen 30. By oblique irradiation from two sides, oblique errors present in different orientations can be detected by at least one probe 32.

FIG. 3 shows a cylindrical support 68 with two eccentric, parallel-axis boreholes 26, which are displaced 180° from each other and are located an equal distance from the center. Each borehole contains one probe carrier 28 with one probe 32. The support 68 itself is positioned in a radial borehole 70 of the rotor 20.

In the embodiment of the invention shown in FIG. 4, there are two probes 32 per probe carrier 28 instead of the one probe per carrier in FIG. 3. These are angular probes that cannot be angularly adjusted.

Finally, the example in FIG. 5 shows a support 68 with four uniformly distributed boreholes 26 for a total of four probe carriers 28. Each probe carrier 28 has a probe 32, which cannot be angularly adjusted.

To compensate imbalances due to axial movement of the main piece 34, either a probe carrier 28 is provided in the diametrically opposite borehole 26 of the rotor 20, or a support 68 with at least one probe carrier 28 is provided in a diametrically opposite borehole 70 of the rotor. In both cases the built-in systems have the same construction. During use, the components are adjusted in the same way to compensate imbalances.

I claim:

1. A rotor of an ultrasonic test device capable of rotating about a symmetry axis of a rotationally symmetrical test specimen, comprising: at least one probe carrier held in the rotor, wherein the probe carrier a) is mounted in a radial borehole, b) contains at least one probe, c) is mounted such that the probe carrier can be adjustably moved longitudinally in a direction of a borehole axis of, the borehole and d) is sealed in the borehole, and wherein the at least one probe carrier is positioned inside the borehole such that the at least one probe carrier is rotationally adjustable about the borehole axis.

2. A rotor of an ultrasonic test device capable of rotating about a symmetry axis of a rotationally symmetrical test specimen, comprising: at least one probe carrier held in the rotor, wherein the at least one probe carrier a) is mounted in a radial borehole, b) contains at least one probe, c) is mounted such that the at least one probe carrier can be adjustably moved longitudinally in a direction of a borehole axis of the borehole, and d) is sealed in the borehole, wherein the at least one probe carrier is positioned inside the borehole such that the probe carrier is rotationally adjustable about the borehole axis, and wherein an inclination of the at least one probe can be adjusted about an axis of rotation running transverse to the borehole axis of the borehole of the rotor, the at least one probe having a first screw part located outside of said axis of rotation, said first screw part being associated with a second screw part, which extends in said direction of the borehole axis and is connected with a rotation adjustment device that is accessible from outside of the at least one probe carrier.

3. The rotor in accordance with claim 1, wherein the borehole is disposed in the rotor and the at least one probe carrier is mounted in the borehole such that the probe carrier fills the borehole.

4. The rotor in accordance with claim 1, wherein the rotor includes a radial borehole, a support being mounted in the radial borehole, and the support has a second radial borehole for the at least one probe carrier.

5. The rotor in accordance with claim 1, wherein the at least one probe carrier has a main piece, a flange and a counterpart, wherein the probe is mounted on the main piece, the main piece has threading in a direction opposite to the probe, the counterpart has a corresponding axial threaded part which engages said threading, and the flange is connected with the main piece in a torsionally rigid way via a variable-length coupling.

6. The rotor in accordance with claim 5, wherein the flange comprises a disk and a ring, the ring is rigidly mounted and forms a guide for rotation of the counterpart, a driver of the coupling is mounted on the disk, and a locking device is provided between the ring and the disk.

7. The rotor in accordance with claim 1, comprising probe carriers of a same construction, mounted in two diametrically opposite boreholes of a same construction.

8. An ultrasonic test device for a test specimens having a specimen axis of rotational symmetry, comprising:
a rotor capable of rotating about the specimen axis, including a radially extending rotor borehole;
a probe carrier containing a probe;
means mounting the probe carrier within the rotor borehole, including first means for adjusting a longitudinal position of the probe carrier in the rotor borehole and second means for adjusting a rotational position of the probe carrier in the rotor borehole.

9. The test device of claim 8, wherein the probe carrier includes third means for adjusting an inclination of the probe about an axis of rotation running transverse to an axis of the borehole.

10. The test device of claim 9, wherein the third means includes a first screw part located outside the axis of rotation, a second screw part associated with the first screw part and extending, and a rotation adjustment device coupled to the second screw part and accessible outside the probe carrier.

11. The test device of claim 8, wherein the probe carrier includes a fluid seal between a peripheral wall of the probe carrier and a surface of the rotor borehole, and wherein the probe carrier substantially fills the rotor borehole.

12. The test device of claim 11, wherein the probe carrier includes a main piece, the probe being mounted on the main piece, the main piece including threading in the opposite direction to the probe, and wherein the means mounting the probe carrier includes a counterpart that comprises an axial threaded part engaging with the threading of the main piece, a flange and fourth means for providing a torsionally rigid variable-length coupling between the flange and the main piece.

13. The test device of claim 12, wherein the flange comprises a disk capable of rotation, a rigidly mounted ring and a locking device for locking the disk to the ring at a selected rotational position.

14. The test device of claim 12, wherein the probe carrier includes third means for adjusting an inclination of the probe about an axis of rotation running transverse to an axis of the borehole.

15. The test device of claim 14, wherein the third means includes a first screw part located outside the axis of rotation, a second screw part associated with the first screw part and extending, and a rotation adjustment device coupled to the second screw part and accessible outside the probe carrier.

16. The test device of claim 8, wherein the means mounting the probe carrier includes a support mounted in the rotor borehole, the support comprising a plurality of support boreholes each capable of holding said probe carrier.

* * * * *

UNITED STATES PATENT AND TRADEMARK OFFICE
CERTIFICATE OF CORRECTION

PATENT NO. : 5,402,682
DATED : April 4, 1995
INVENTOR(S) : Ottokar Patzke

It is certified that error appears in the above-indentified patent and that said Letters Patent is hereby corrected as shown below:

Column 5, line 31,

Claim 1, line 8, after the word "of", delete ",".
Column 5, line 31,
Claim 1, line 8, after the word "borehole", insert —,—.
Column 5, line 45,
Claim 2, line 11, before the word "probe", insert — the at least one —.
Column 6, line 14,
Claim 8, delete "specimens" and insert therefor — specimen —.

Signed and Sealed this

Eighth Day of August, 1995

Attest:

BRUCE LEHMAN

*Attesting Officer*      *Commissioner of Patents and Trademarks*